(12) United States Patent
Jinton

(10) Patent No.: US 11,246,686 B2
(45) Date of Patent: Feb. 15, 2022

(54) SCREWDRIVER AND SCREW FOR MEDICAL APPLICATIONS, IN PARTICULAR FOR DENTAL APPLICATIONS

(71) Applicant: NEOSS LIMITED, Harrogate (GB)

(72) Inventor: Lars Jinton, Mölndal (SE)

(73) Assignee: Neoss Limited, Harrogate (GB)

( * ) Notice: Subject to any disclaimer, the term of this patent is extended or adjusted under 35 U.S.C. 154(b) by 0 days.

(21) Appl. No.: 16/093,490

(22) PCT Filed: Apr. 12, 2017

(86) PCT No.: PCT/GB2017/051017
§ 371 (c)(1),
(2) Date: Oct. 12, 2018

(87) PCT Pub. No.: WO2017/178815
PCT Pub. Date: Oct. 19, 2017

(65) Prior Publication Data
US 2019/0167388 A1 Jun. 6, 2019

(30) Foreign Application Priority Data
Apr. 14, 2016 (EP) .................... 16165389

(51) Int. Cl.
*A61C 8/00* (2006.01)
*A61B 17/86* (2006.01)
*A61B 17/88* (2006.01)

(52) U.S. Cl.
CPC ........ *A61C 8/0089* (2013.01); *A61B 17/8615* (2013.01); *A61B 17/888* (2013.01); *A61B 17/8888* (2013.01); *A61C 8/0018* (2013.01)

(58) Field of Classification Search
CPC ............. A61C 8/0089; A61C 8/00189; A61C 8/0018; A61B 17/8615; A61B 17/888;
(Continued)

(56) References Cited

U.S. PATENT DOCUMENTS 4,598,011 A 7/1986 Bowman
5,032,445 A 7/1991 Scantlebury et al.
(Continued)

FOREIGN PATENT DOCUMENTS

DE 4414675 C1 9/1995
EP 0747017 A2 12/1996
(Continued)

OTHER PUBLICATIONS

Extended European Search Report dated Oct. 10, 2016 for EP Application No. 16165389.4; 8 pages.
(Continued)

*Primary Examiner* — Nicholas D Lucchesi
*Assistant Examiner* — Mirayda A Aponte
(74) *Attorney, Agent, or Firm* — Shay Glenn LLP

(57) ABSTRACT

A screwdriver for medical, in particular dental applications, is provided, the screwdriver (2, 2', 2") being configured to cooperate with a screw (1, 1'), the screw (1, 1') having an apical end (11), a coronal end (10), a screw axis (S) and a first recess (14) at the coronal end for engagement with the screwdriver, the first recess (14) having a substantially polygonal inner contour in a radial plane that is perpendicular to the screw axis (S), the screwdriver (2, 2', 2") comprising a shaft (2) defining a longitudinal axis (D) of the screw driver, and an engagement portion (21, 21', 21") for engagement with the first recess (14) of the screw (1, 1'), the engagement portion (21, 21', 21") having a substantially polygonal outer contour with corners (23, 23', 23") and outer surfaces (22, 22', 22") between the corners (23, 23', 23") wherein in a radial plane that is perpendicular to the longitudinal axis (D), the outer surfaces (22, 22', 22") between two neighbouring corners (23, 23', 23") are curved radially outward.

10 Claims, 6 Drawing Sheets

(58) Field of Classification Search
CPC ............ A61B 17/8888; A61B 17/7082; A61B 17/861; A61B 17/8875; A61B 17/8605; A61B 17/86; A61B 17/84; A61B 17/68; A61B 17/58; A61B 17/56; F16B 35/00; F16B 35/04; F16B 35/044; F16B 35/042; F16B 23/0038; F16B 35/041; F16B 35/045; B25B 13/065; B25B 13/06; B25B 23/0035; B25B 23/108
USPC ......................................................... 433/141
See application file for complete search history.

(56) References Cited

U.S. PATENT DOCUMENTS

| | | | |
|---|---|---|---|
| 5,093,179 | A | 3/1992 | Scantlebury et al. |
| 5,380,328 | A | 1/1995 | Morgan |
| 5,873,721 | A | 2/1999 | Willoughby |
| 6,131,493 | A * | 10/2000 | Yamamoto ............ B25B 13/065 81/121.1 |
| 6,619,958 | B2 | 9/2003 | Beaty et al. |
| 8,556,990 | B2 | 10/2013 | Bartee et al. |
| 10,238,497 | B2 | 3/2019 | Engman |
| 2005/0166724 | A1 | 8/2005 | Castaneda |
| 2006/0224242 | A1 | 10/2006 | Swords et al. |
| 2007/0037122 | A1 | 2/2007 | Bassett et al. |
| 2007/0281279 | A1 | 12/2007 | Chander |
| 2008/0044449 | A1 | 2/2008 | McKay |
| 2008/0254414 | A1 | 10/2008 | McGuire et al. |
| 2010/0143071 | A1 * | 6/2010 | Ishikawa ................ A61C 8/005 411/403 |
| 2010/0167240 | A1 | 7/2010 | Benzon et al. |
| 2011/0207083 | A1 | 8/2011 | Boehm-Van Diggelen |
| 2011/0306014 | A1 | 12/2011 | Conte et al. |
| 2013/0103054 | A1 | 4/2013 | Housman |
| 2013/0288199 | A1 | 10/2013 | Wen |
| 2014/0134570 | A1 * | 5/2014 | Zipprich ................ A61C 8/005 433/173 |
| 2014/0205969 | A1 | 7/2014 | Marlin |
| 2015/0289905 | A1 * | 10/2015 | Biedermann ...... A61B 17/8615 606/270 |
| 2016/0022390 | A1 | 1/2016 | Spindler et al. |

FOREIGN PATENT DOCUMENTS

| | | | | |
|---|---|---|---|---|
| EP | 2053985 | B1 | 5/2010 | |
| EP | 2343025 | A2 | 7/2011 | |
| EP | 2478864 | A2 * | 7/2012 | ........... A61C 8/0018 |
| EP | 2478864 | A2 | 7/2012 | |
| EP | 2526893 | A1 | 11/2012 | |
| EP | 3378434 | A1 | 9/2018 | |
| JP | 2004236767 | A | 8/2004 | |
| KR | 10731541 | B1 | 5/2017 | |
| WO | WO2011/125760 | A1 | 10/2011 | |
| WO | WO2013/004386 | A1 | 1/2013 | |
| WO | WO2013/004387 | A1 | 1/2013 | |
| WO | WO-2013004386 | A1 * | 1/2013 | ........... A61C 8/0001 |
| WO | WO2013/112233 | A1 | 8/2013 | |
| WO | WO2014/198682 | A1 | 12/2014 | |
| WO | WO2017/002111 | A1 | 1/2017 | |
| WO | WO2017/072066 | A1 | 5/2017 | |

OTHER PUBLICATIONS

3 Shape; Impress your patents with shape TRIOS: Intraoral scanners; 12 pages as availiable on Aug. 17, 2017; retrieved from the internet (https://web.archive.org/web/20170817214137/http://www.3shape.com/products/trios/intraoral-scanners) ; on Mar. 4, 2020.

International Preliminary Report on Patentability dated Jun. 18, 2019 for PCT/EP2016/081580; 10 pages.

International Search Report and Written Opinion dated Feb. 25, 2019 for PCT/GB2018/052265; 23 pages.

Jinton; U.S. Appl. No. 16/464,193 entitled "Dental abutment black, method of manufacturing a dental abutment blank and method of manufacturing a dental prosthesis from such a blank," filed May 24, 2019.

Engman; U.S. Appl. No. 16/628,279 entitled "Dental implant assembly," filed Jan. 3, 2020.

European Search Report dated Mar. 23, 2020 for EP 16823235.3; 5 pages.

\* cited by examiner

SCREWDRIVER AND SCREW FOR MEDICAL APPLICATIONS, IN PARTICULAR FOR DENTAL APPLICATIONS

TECHNICAL FIELD

The invention relates to a screwdriver and a screw for medical applications, in particular for dental applications, such as fastening a dental component to a dental implant. The screwdriver has a design that increases the contact surfaces allowing a higher tightening torque to be used when fastening a dental component to a dental implant. The screwdriver and screw also include a screw lifting function and/or pivoting function enabling to lift the screw and/or to pivot the screwdriver at an angle relative to the screw axis.

BACKGROUND OF THE INVENTION

A screw retained dental prosthesis is fastened to a dental implant with one or several screws depending on the prosthesis design. The fastening screw is inserted through an access bore in the prosthesis. To hold the prosthesis in place, a high tightening torque is required to prevent the prosthesis from becoming loose when exposed to loads from biting and chewing during use. Due to the small dimensions of the fastening screws, it is essential to be able to apply a high tightening torque without overloading/deforming an engagement recess also called screw grip of the screw for engagement with the screwdriver.

Referring to FIGS. 13a to 14, a conventional screw 100 comprises a polygonal, for example hexagonal recess 101, that is engaged by a screwdriver (or wrench tool) with a polygonal, for example hexagonal, engagement portion 201 having corners 202 defining the polygon. As illustrated in FIG. 13a, a clearance 300 is required between the polygonal engagement portion 201 and the polygonal recess 101 to ensure the engagement. When a torque is applied as shown in FIG. 13b, the clearance 300 allows the engagement portion 201 to rotate in the recess 101. This rotation limits the contact surface to the corners 202 of the engagement portion 201. High stress concentrations are applied to the corners 202 which can result in damages such that material at the corners 202 may shear off or in that the recess 101 may be deformed or damaged at the contact area.

Referring further to FIG. 15, a screwdriver 200 is known that has a tapered engagement portion 201. The tapered engagement portion 201 engages the polygonal recess 101 of the screw 100 at contact areas 400. Due to the tapered shape, a wedging between the tapered engagement portion 201 and the recess 101 takes place that allows the screw to be lifted and carried by the screwdriver to the prosthesis in the patient's mouth. As the contact between the engagement portion 201 of the screwdriver and the recess 101 is along the opening edge of the polygon recess there is a risk that the recess 101 is deformed due to stress concentrations.

Dependent on the anatomy, bone volume and operator skills, implants are not always optimally positioned thus resulting in difficulties accessing the prosthetic screw or in the requirement to apply a cemented solution over a more favourable screw-retained solution. One way to overcome these positioning issues is to offer a restoration with an angulated screw access hole which receives a screw to be positioned and tightened and retrieved with a screwdriver at an angle to the screw axis. A screwdriver permitting such an angled access is described, for example, in US 2010/0167240 A1.

SUMMARY OF THE INVENTION

It is the object of the invention to provide a screwdriver and a combination of a screwdriver and a screw as well as a screw suitable for use with the screwdriver that permit an improved fixation and handling.

The object is solved by a screwdriver according to claim 1, and a combination of a screwdriver and a screw according to claims 6 and 8. Further developments are given in the dependent claims.

According to one aspect of the invention, a screwdriver for medical, in particular dental applications, is provided the screwdriver being configured to cooperate with a screw, the screw having an apical end, a coronal end, a screw axis and a first recess at the coronal end for engagement with the screwdriver, the first recess having a substantially polygonal inner contour in a radial plane that is perpendicular to the screw axis, the screwdriver comprising a shaft defining a longitudinal axis of the screw driver, and an engagement portion for engagement with the first recess of the screw, the engagement portion having a substantially polygonal outer contour with corners and outer surfaces between the corners wherein in a radial plane that is perpendicular to the longitudinal axis, at least a proportion of the outer surfaces between two neighbouring corners are curved radially outward.

According to this aspect, the outer surfaces of the engagement portion of a polygonal screwdriver are curved instead of flat. This results in the clearance between the engagement portion of the screwdriver being increased at the corners and reduced in the center of a sidewall of the polygonal first recess of the screw. Hence, the load applied during tightening will be transferred over a larger surface area and not only over the corners of the polygonal engagement portion. When torque is applied, the curved surfaces will at contact align more perpendicular to the sidewalls of the polygon recess of the screw resulting in a larger contact area which distributes the load more evenly and reduces the stress concentration at the corners.

The outer surfaces may, in the radial plane, be curved in a continuous arc shape and/or may have a shape of a segment of a circle. Not only a proportion of the outer surface between two corners but the entire outer surface between two corners may be curved radially outward.

The outer surfaces may comprise, in the radial plane, at least two straight portions that are connected to each other and that include an obtuse angle with each other, preferably an angle that is greater than an angle of neighbouring corners that define the polygon of the engagement portion.

The engagement portion of the screwdriver may have a free end opposite to the shaft and at least a portion of the engagement portion may taper towards the free end to permit holding of the screw when engaging the first recess.

A screwdriver having the tapered engagement portion increases in size as it is inserted in the polygonal first recess of the screw. The contact and friction between the engagement portion of the screwdriver and the first recess of the screw allows the screw to be lifted and carried by the screwdriver. With the tapered engagement portion with the curved surfaces a lifting function is enabled by a wedging action between the first recess of the screw and the engagement portion of the screwdriver. The risk for deforming the first recess of the screw due to stress concentration is reduced.

The engagement portion may have in a plane including the longitudinal axis of the shaft at least a portion with a rounded outer contour, preferably a ball-shaped contour, to permit pivoting in the first recess of the screw.

By such a rounded, more specifically ball-shaped design to the engagement portion of the screwdriver, it is possible to pivot or rotate the screwdriver at an angle relative to the screw axis. The ball-shaped design of the engagement portion with the curved surfaces of the polygon enables the screwdriver to pivot or rotate at an angle relative to the screw axis while maintaining contact with the first recess of the screw thereby enabling a lifting function also at an angle.

According to another aspect, a combination of a screwdriver and a screw for medical, in particular dental applications, may include a screwdriver as described above and a screw, the screw having an apical end, a coronal end, a screw axis and a first recess at the coronal end for engagement with the screwdriver, the first recess having a substantially polygonal inner contour in a radial plane that is perpendicular to the screw axis, wherein sidewalls between neighbouring corners of the first recess are substantially flat and extend substantially parallel to the screw axis.

In the combination the engagement portion and the first recess may be sized such that when the engagement portion engages the first recess and the corners of the polygon of the engagement portion are aligned with the corners of the polygon of the first recess the clearance between the sides of the polygon of the first recess and the sides of the polygon of the engagement portion is greater in a region adjacent to the corners than at a distance from the corners.

The engagement portion of the screwdriver of the combination may have a free end and at least a portion of the engagement portion may taper towards the free end and wherein when the engagement portion engages the first recess and the corners of the polygon of the first recess are aligned with the corners of the polygon of the screwdriver a contact between the engagement portion and the first recess is established that permits to hold the screw with the screwdriver.

The screw in the combination may comprise a plurality of second recesses that are provided in the sidewalls of the first recess and that taper from the coronal end of the screw in the direction of the apical end.

The combination of the screw having the tapered second recesses of the screwdriver having the tapered engagement portion with the curved outer surfaces provides a lifting function by the wedging action in contact points of the first recess and the engagement portion of the screwdriver. As the engagement portion of the screwdriver is larger than the distance between opposite sidewalls of the polygonal first recess, the curved surfaces will extend into the tapered second recesses of the first recess of the screw. The curved surfaces of the engagement portion of the screwdriver will at the same time enable a clearance in the corners of the first recess of the screw. The polygonal first recess of the screw is not tapered and can be manufactured by stamping which is more cost-effective compared to milling. Also, according to this design, the contact of the engagement portion of the screwdriver with the first recess is at a distance from the opening edge of the first recess in an axial direction which provides a better stress distribution.

A width of the second recesses in the circumferential direction may decrease in the direction towards the apical end.

The second recesses may be provided at substantially the center of each sidewall in a circumferential direction around the screw axis and wherein a width of the second recesses in the circumferential direction is smaller than a width of the sidewalls of the first recess so that an intersection is formed between each sidewall and an associated second recess.

When the engagement portion engages the first recess and the corners of the polygon of the first recess are aligned with the corners of the polygon of the screwdriver the contact between the engagement portion and the first recess is established at contact areas located at the second recesses close to the intersection between the sidewall of the polygons of the first recess and the associated second recess.

The screw may comprise a third recess that extends from the coronal end towards the apical end and that is coaxial with the first recess, wherein the third recess extends radially outward from the sidewalls connecting neighbouring corners of the first recess and may have a substantially circular cross section in a plane perpendicular to the screw axis.

The third recess (or further recesses) can be added to the surfaces of the polygonal first recess to maintain the same clearance all around the engagement portion of the screwdriver. A bore in the center of a polygon is commonly used to reduce the material volume to be removed when stamping the polygon. This reduces the stamping force and simplifies the manufacturing process. As the contact surface area is not positioned in the center of the polygonal first recess adding a third recess in the form of a circular bore, will not affect the load distribution.

The engagement portion may have in a plane including the longitudinal axis of the shaft at least a portion with a rounded outer contour and wherein the engagement portion and the first recess are sized such that when the engagement portion engages the first recess the engagement portion is permitted to pivot in the first recess of the screw.

According to a further aspect, a screw for medical, in particular dental applications, the screw being configured to cooperate with a screwdriver described above, may comprise an apical end, a coronal end, a screw axis and a first recess at the coronal end for engagement with the screwdriver, the first recess having a substantially polygonal inner contour in a radial plane that is perpendicular to the screw axis, wherein sidewalls between neighbouring corners of the first recess are substantially flat and extend substantially parallel to the screw axis; and wherein a plurality of second recesses are provided in the sidewalls of the first recess that taper from the coronal end of the screw in the direction of the apical end.

Further features and advantages of the invention will become apparent from the description of embodiments by means of the accompanying drawings.

BRIEF DESCRIPTION OF THE DRAWINGS

FIG. 11b shows an enlarged view of the detail marked with a circle in FIG. 11a.

DETAILED DESCRIPTION OF EMBODIMENTS

Figure 1:
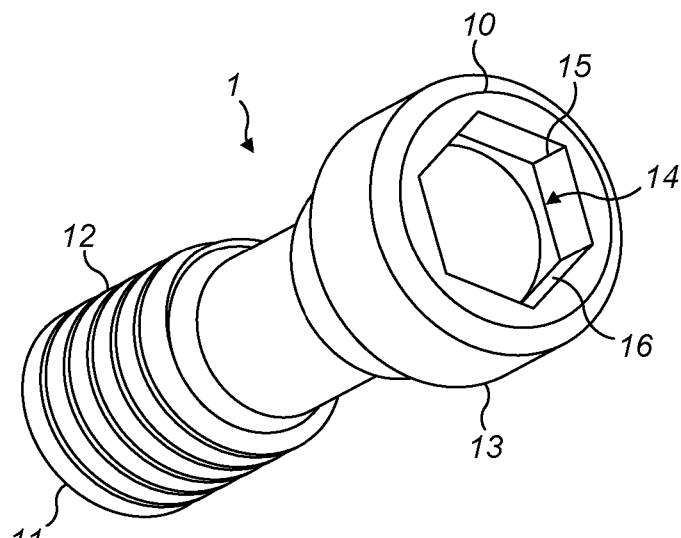
FIG. 1 shows a perspective view of a screw according to an embodiment of a combination of a screwdriver and a screw.

In the embodiment shown in FIGS. 1 to 3b, the screw 1 has a coronal end 10 and an apical end 11 opposite to the coronal end 10. At least a portion of the screw 1 is provided with a thread 12 defining a screw axis S. Adjacent to the coronal end 10, the screw has a head 13. The head 13 may be, for example, cylindrical or otherwise shaped. In the free end surface of the coronal end 10, a first recess 14 is provided that has in a radial plane that is perpendicular to the screw axis S a polygonal contour, for example a hexagonal contour. The first recess 14 forms a screw grip. By the first recess 14, corners 15 are formed where adjacent sidewalls 16 of the recess 14 meet. The sidewalls 16 are substantially flat and straight, i.e. extend parallel to the screw axis S. The corners 15 may be defined by two adjacent sidewalls 16 meeting directly or meeting via radii. In other words, the corners 15 may be sharp or rounded. Below the first recess 14 in a direction towards the apical end 11, a bore 17 with an inner diameter that may be greater than the distance between opposite corners 15 of the first recess 14 may be provided. The bore 17 may be followed by a hollow cone-shaped bottom section 18. The bore 17 and the cone-shaped bottom section 18 may be used to permit the screwdriver to extend partially therein.

Figure 2:
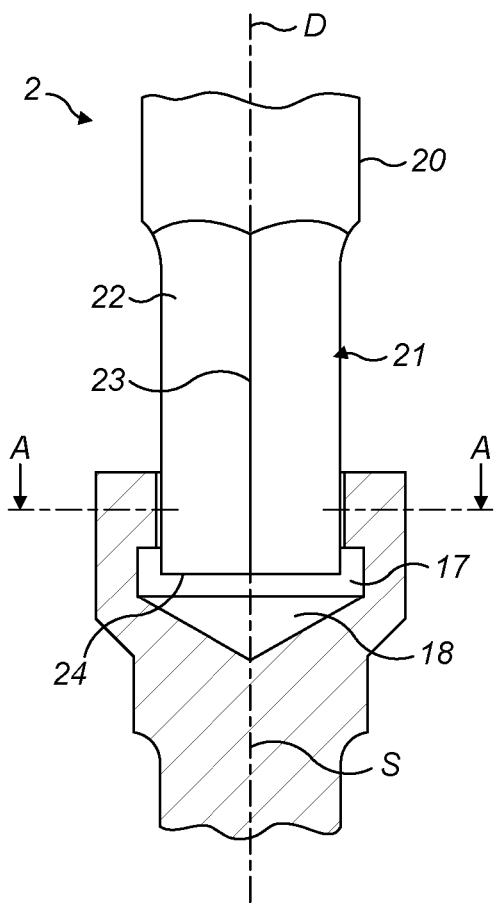
FIG. 2 shows a cross-sectional view of the upper portion of the screw and the engagement portion of the screwdriver in engagement with the polygonal recess of the screw, the cross-section taken in a plane including the screw axis.

The screwdriver 2 according to an embodiment comprises a shaft 20 and a front end portion that forms an engagement portion 21 for engaging the first recess 14 of the screw 1. A central longitudinal axis forms a drive axis D of the screwdriver 2. As shown more in detail in FIGS. 3a and 3b, the engagement portion 21 has in a cross-sectional plane that is perpendicular to the drive axis D a substantially polygonal outer contour with sides between neighbouring corners 23 that are curved radially outward with respect to a line that connects neighbouring corners. More specifically, the sides may be curved outward in an arc-shape, in particular in a circular segment-shaped fashion. Three-dimensionally, the sides form outwardly curved outer surfaces 22 of the engagement portion 21. In this embodiment, the corners 23 have in an axial direction along a length that corresponds to at least a depth of the first recess 14 of the screw, preferably along a length up to a free end 24 of the engagement portion 21, a substantially constant distance from the drive axis (FIG. 2). The corners 23 may be sharp, i.e. the outer curved surfaces 22 meet each other directly, or rounded, i.e. the outer curved surfaces meet each other via radii. The number of corners 23 corresponds to the number of corners 15 of the first recess 14 of the screw. Preferably, the polygonal shape of recess 14 and engagement portion is a hexagon.

Figure 3A:
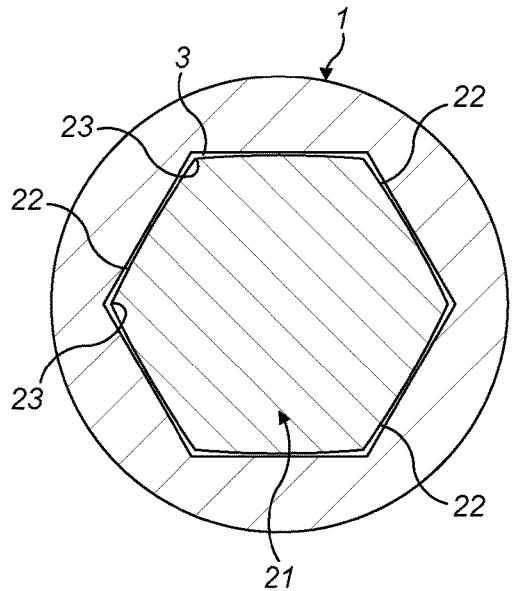
FIG. 3a shows a cross-sectional view of the embodiment of FIGS. 1 and 2 along line A-A in FIG. 2 in an aligned configuration of the engagement portion of the screwdriver with the polygonal recess of the screw.

The radius of curvature of the outer surface 22 is selected in such a way that when the engagement portion 21 is inserted into the recess 14 of the screw 1 and the corners 23 of the engagement portion 21 are aligned with the corners 15 of the first recess 14 as shown in FIG. 3a, there is a clearance 3 between the outer surfaces 22 and the sidewalls 16 of the recess 14 that is smallest in the center between two corners 15 and increases towards the corners 15 of the first recess 14 of the screw 1. The radius of the curvature may vary depending on the size of the first recess 14, in particular the radius of the curvature may increase as the size of the first recess increases. The relationship between the clearance 3 at the center of the curved outer surfaces 22 and at the corners 23 in a radial plane may be substantially the same for different sizes of the first recess 14 and the corresponding engagement portion 21.

Figure 3B:
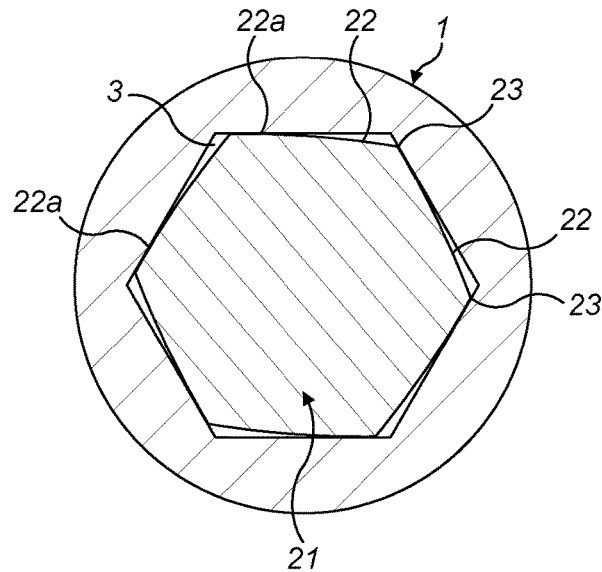
FIG. 3b shows a cross-sectional view of the embodiment of FIGS. 1 and 2 along line A-A in FIG. 2 in a rotated configuration of the engagement portion of the screwdriver with the polygonal recess of the screw.
Figure 13A:
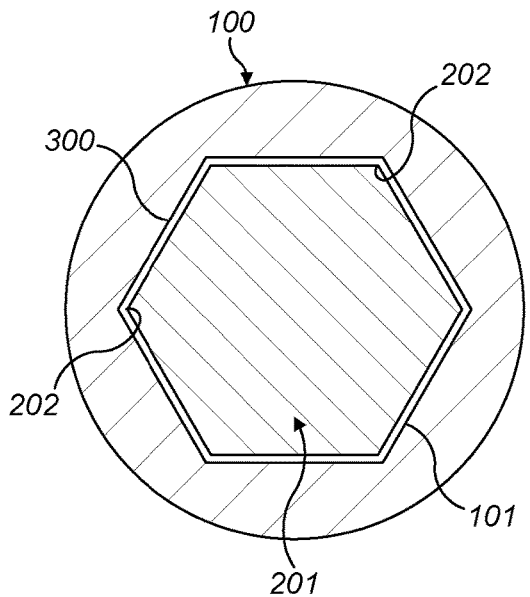
FIG. 13a shows a cross-sectional view of a conventional combination of a polygonal recess of a screw with a polygonal screwdriver in an aligned configuration, the cross-section taken in a plane perpendicular to the screw axis.
Figure 13B:
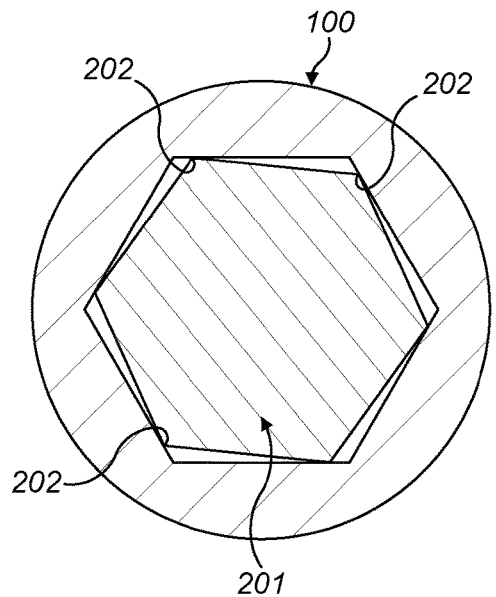
FIG. 13b shows the combination of FIG. 13a in a rotated configuration of the screwdriver relative to the recess of the screw.
Figure 14:
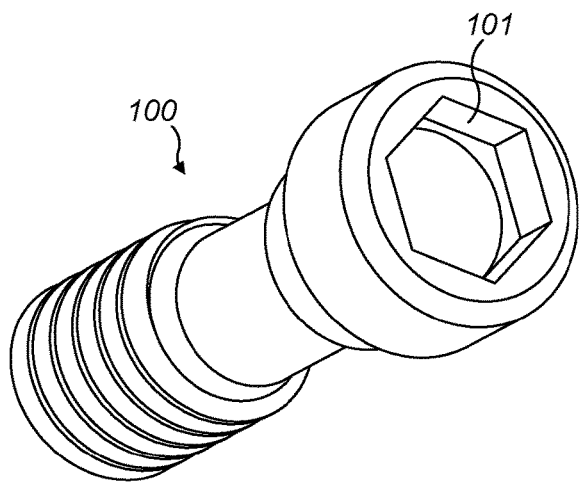
FIG. 14 shows a perspective view of a conventional screw with a hexagon recess for the screwdriver.
Figure 15:
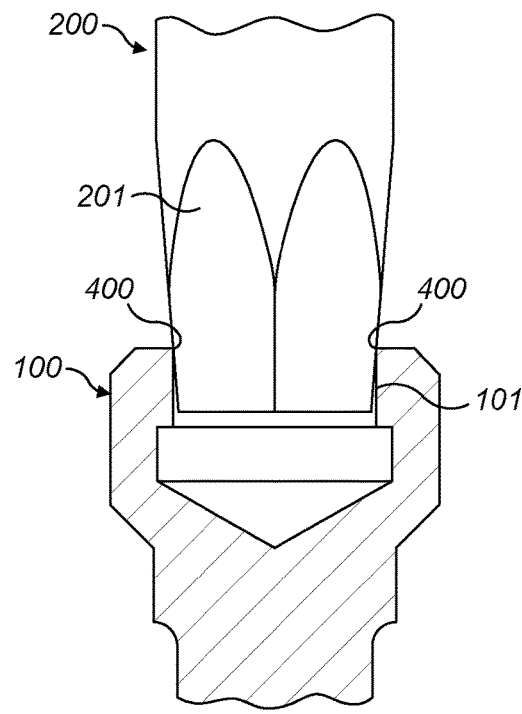
FIG. 15 shows a cross-sectional view of a combination of a conventional screw with a conventional screwdriver having a tapered engagement portion, the cross-section taken in a plane containing the screw axis.

When torque is applied with the screwdriver as shown in FIG. 3b, the engagement portion 21 rotates slightly before coming into contact with the sidewalls 16 of the recess 14. The curved surfaces 22 will at contact align to the sidewalls 16 of the recess 14 resulting in a larger contact area 22a. In relation to the known design shown in FIG. 13b, the alignment is more perpendicular. The load applied during tightening will be transferred over the larger contact surface area 22a of the curved outer surfaces 22. Compared to conventional screwdrivers, where the load is transferred over the corners of the polygon, the risk of deforming the screw grip due to stress concentrations is reduced. Therefore, high tightening torques can be applied without overloading/deforming the screw grip. As a result, the prosthesis can be held in place more safely and is prevented from becoming loose when exposed to loads from biting and chewing during use. Fastening screws with small dimensions can be used.

Figure 4A:
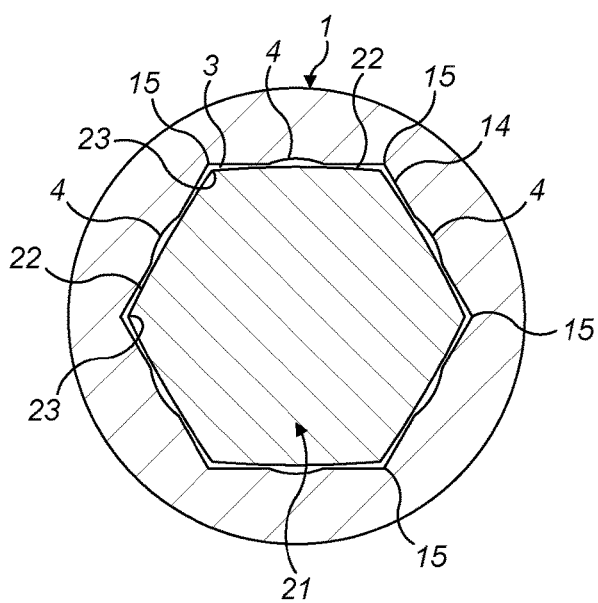
FIG. 4a shows a cross-sectional view of another embodiment of the combination of the screwdriver with the polygonal recess of the screw, the cross-section taken in a plane perpendicular to the screw axis, in an aligned configuration of the engagement portion of the screwdriver with the polygonal recess of the screw.
Figure 4B:
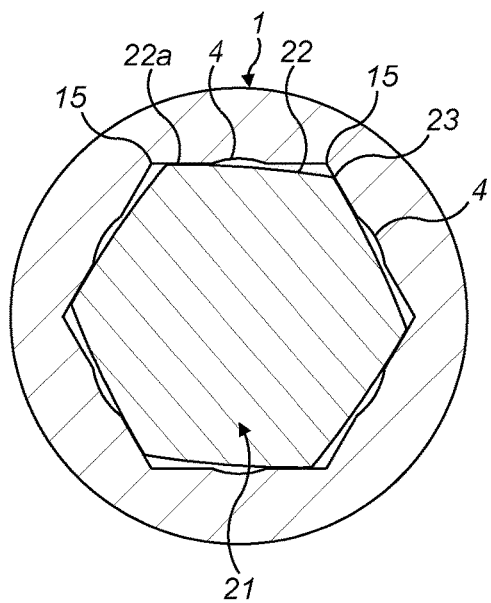
FIG. 4b shows a cross-sectional view of the embodiment of FIG. 4a in a rotated configuration of the engagement portion of the screwdriver with the polygonal recess of the screw.

In a second embodiment, as shown in FIGS. 4a and 4b, recesses 4 can be added to the sidewalls 16 of the first recess 14 of the screw 1. The recesses 4 can be obtained by providing a bore with a circular cross-section in the center of the coronal end 10 of the screw that is commonly used to reduce the material volume to be removed when stamping the polygonal first recess 14. Hence, the bore forms the recesses 4 with a circular segment-shaped contour in a plane perpendicular to the screw axis S. The recesses 4 are preferably in the center of each sidewall 16. When load is applied during tightening the screw with the screwdriver, as depicted in FIG. 4b, the contact surface area 22a is not positioned in the center of the sidewall 16. Therefore, the adding of the recesses 4 will not affect the load distribution.

It shall be noted that the recesses 4 may also have another shape and/or position and need not to be provided by a central bore with a circular cross-section.

Figure 5:
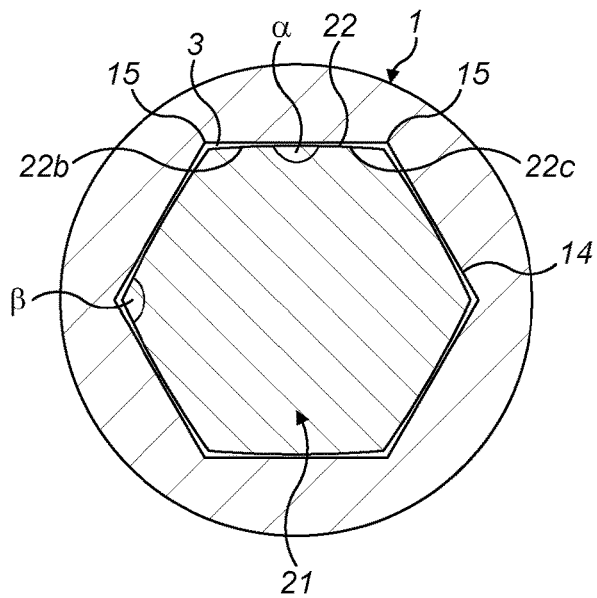
FIG. 5 shows a cross-sectional view of still another embodiment of the combination of the screwdriver with the polygonal recess of the screw, the cross-section taken in a plane perpendicular to the screw axis, in an aligned configuration of the engagement portion of the screwdriver with the polygonal recess of the screw.
Figure 6:
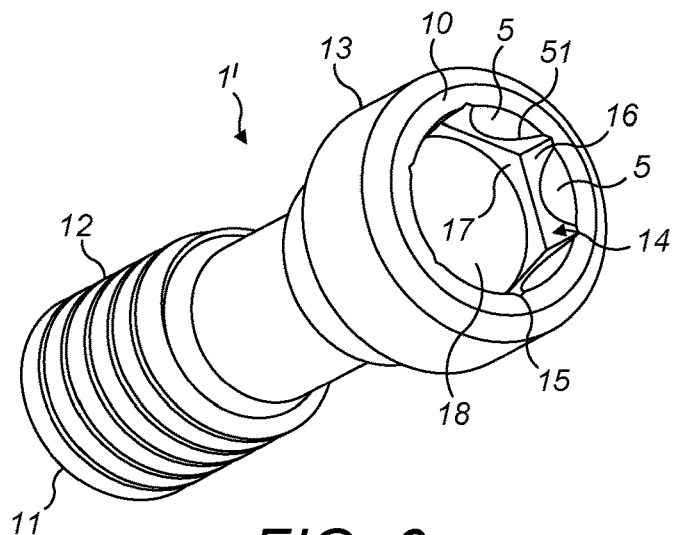
FIG. 6 shows a perspective view of a screw according to an embodiment.
Figure 7:
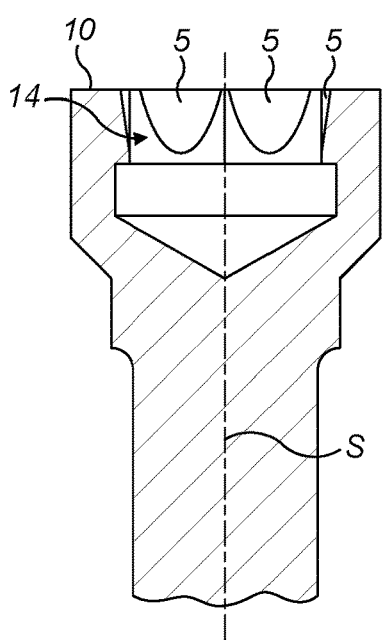
FIG. 7 shows a cross-sectional view of the screw of FIG. 6, the cross-section taken in a plane containing the screw axis.
Figure 8:
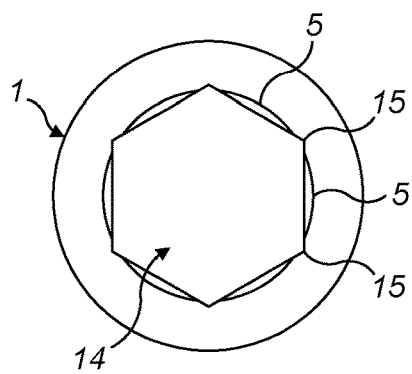
FIG. 8 shows a top view of the screw of FIG. 6.

Referring to FIG. 5, a further embodiment will be described. A curved outer surface 22 of the engagement portion 21 of the screwdriver 2 may also be achieved by dividing the surface between neighbouring corners 23 into two or more slightly angled surfaces 22b, 22c that meet at an obtuse angle α. In the case of two flat surfaces 22b, 22c, the surfaces meet in the middle between two adjacent corners 23 in the circumferential direction. The obtuse angle α is preferably greater than an angle β that defines the polygon of the engagement portion 21. The embodiment depicted in FIG. 5 provides the same function as the embodiment of FIG. 1 with a circular curvature.

Referring to FIGS. 6 to 11b, a still further embodiment of a screw and the cooperation of a screwdriver with the screw will be described. The screw 1' differs from the screw shown in FIG. 1 by the design of the recess for engagement with the screwdriver. Parts and portions that identical or similar to those of the screw shown in FIG. 1 have the same reference numerals and the description thereof will not be repeated.

The screw 1' comprises in addition to the first recess 14 for engagement with the screwdriver 2 a plurality of second recesses 5. The second recesses 5 are provided in each sidewall 16, respectively, of the first recess 14 and are each symmetrical about an axis extending though the center between two adjacent corners 15 and parallel to the screw axis S. As can be seen more in detail in FIG. 7, the second recesses 5 taper in a direction from the coronal end 10 towards the apical end 11 of the screw 1'. Therefore, a total width of the first recess 14 between opposite side walls 16 in the region of the second recesses 5 is greater at the coronal end 10 than at a distance thereof in direction to the apical end 11. A width of the second recesses 5 in the circumferential direction at the coronal end 10 is slightly smaller than a width of the straight sidewalls 16 of the recess 14. An intersection 51 is formed between each sidewall 16 and an associated second recess 5. Moreover, a width of the second recesses 5 in the circumferential direction may decrease in the direction towards the apical end 11. In the embodiment, the tapered second recesses 5 have a cylinder segment shape with the axis of the cylinder intersecting the screw axis S. Thus the intersection 51 between the recesses 5 and the sidewalls 16 has the shape of a parabola. The tapered second recesses 5 can also have another, preferably outwardly curved shape and the intersection 51 can also have another shape, for example a V-shape or U-shape. If a V or a U shape is selected for the recesses 5, the contact points 53 along the intersection 51 will move. Therefore, by selection a shape for the recesses 5 the contact points 53 may be obtained at desired positions that may be optimized in view of the distribution of stresses or in view of other mechanical properties.

Figure 9:
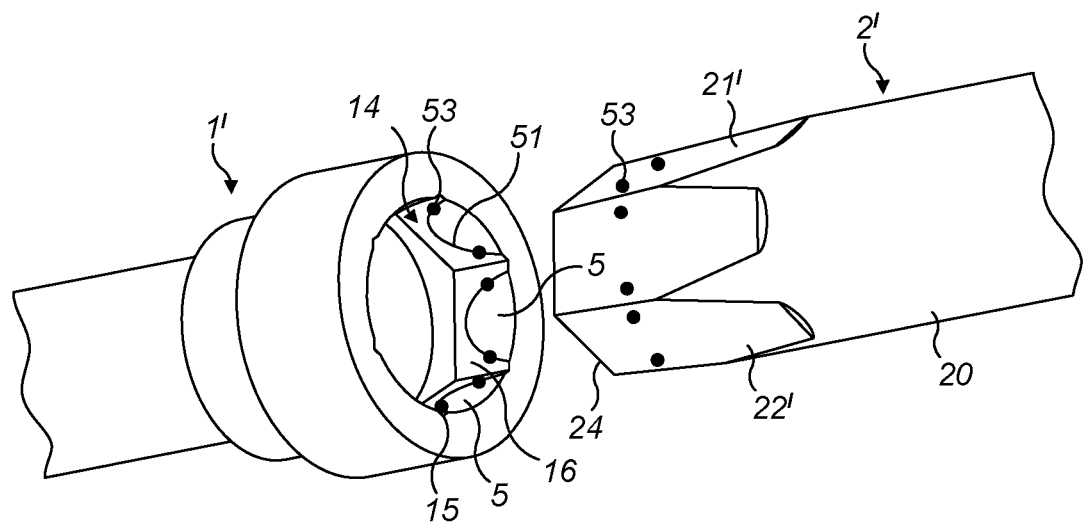
FIG. 9 shows a perspective exploded view of a further embodiment of the combination of a screwdriver and a screw that comprises the screw of FIGS. 6 to 8 with a further embodiment of a screwdriver.

A screwdriver 2' according to a second embodiment differs from the screwdriver of the first embodiment by the design of the engagement portion. The engagement portion 21' of the screwdriver 2' comprises at least a portion that tapers towards the free end 24. Hence, in an axial direction, the distance of the corners 23' from the drive axis D decreases towards the free end 24. Preferably, the corners 23' lie on a cone that narrows towards the free end 24. As in the previous embodiment, the outer surfaces 22' between the corners 23 are outwardly curved. When the tapered engagement portion 21' is inserted into the recess 14, the outer contour increases in size as the engagement portion 21' is inserted into the first recess 14. The contact and the friction between the engagement portion 21' and portions in the recess 14 will enable the screw to be lifted and carried by the screwdriver. As shown in FIG. 9, the engagement portion 21' will engage with the first recess 14 in contact points 53 or contact areas located at the intersection 51 between the straight flat sidewalls 16 and the tapered recesses 5 explained below.

Figure 10:
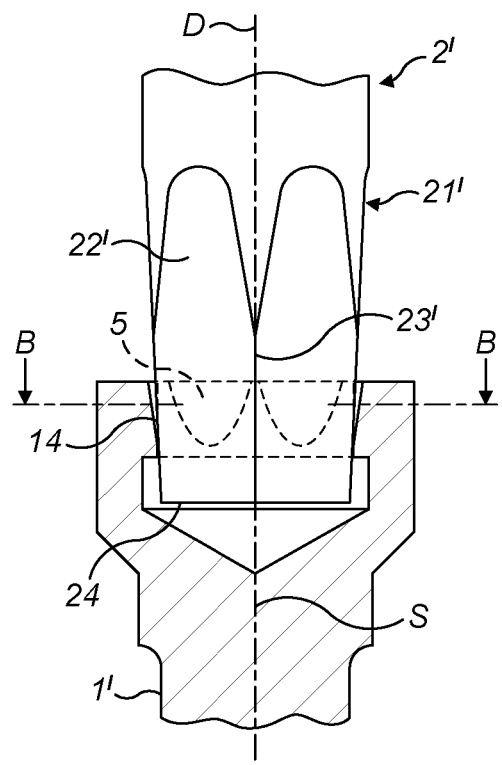
FIG. 10 shows a cross-sectional view of the combination of FIG. 9 in an engaged configuration, the cross-section taken in a plane including the screw axis.
Figure 11A:
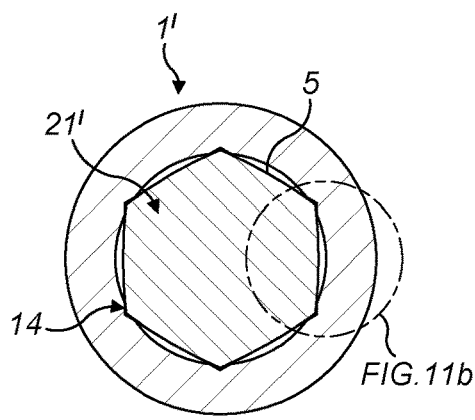
FIG. 11a shows a cross-sectional view of the combination of FIG. 10, the cross-section taken along line B-B in FIG. 10.
Figure 11B:
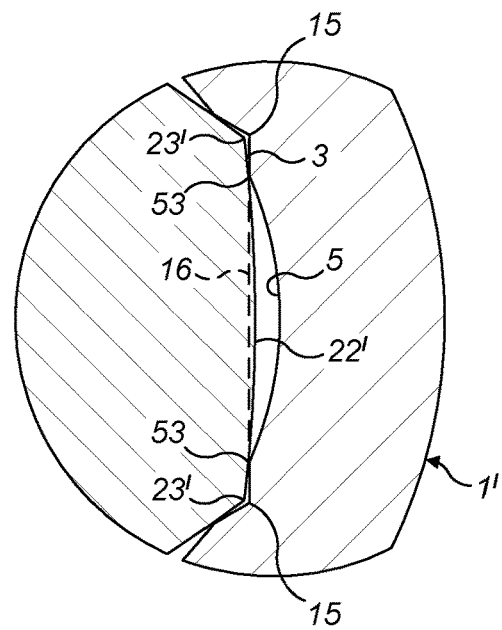

Referring to FIG. 10 to FIG. 11b, the interaction between the engagement portion 21' of the screwdriver 2' and the recess 14 of the screw 1' is shown in more detail. In FIG. 10 the line between B-B shows the axial plane at the contact level between the tapered engagement portion 21' and sidewalls 16 of the recess 14 of the screw P. As the engagement portion 21' is greater than the polygon of the first recess 14 defined by the straight sidewalls 16, the curved surfaces 22' of the engagement portion 21' will extend into the tapered second recesses 5 of the first recess 14. At the same time, the curved surfaces 22' will enable a clearance 3 in the corners 15 of the first recess 14. In other words, the engagement portion 21' can be described as being larger in the center and smaller in the corners 23' when compared to the recess 14 of the screw. FIG. 11a shows the cross-section of the combination of the screwdriver 2' and the screw 1' at the contact level. In FIG. 11b, that shows an enlarged detail of FIG. 11a, the dashed line illustrates the straight sidewalls 16 of the first recess 14 of the screw P. The outwardly curved surfaces 22' of the engagement portion are at the contact level partially larger than the line of the sidewalls 16 of the first recess 14 of the screw 1' and extend into the tapered second recesses 5. This results in the contact points 53 along the intersection of the tapered recesses 5 with the sidewalls 22' of the engagement portion 21'. A lifting function is enabled by a wedging action in the contact points 53 of the first recess 14 and the engagement portion 21'.

In use, when the first recess 14 of the screw 1' is engaged by the engagement portion 21' of the screwdriver 2' and when a wedging takes place at the contact points 53, the screw 1' is lifted and can be carried by the screwdriver 2'. When the screw 1' shall be tightened, the screwdriver 2' rotates and the contact area is larger compared to a conventional design. Therefore, the load is more evenly distributed and stress concentrations at the corners are reduced. Moreover, the engagement between the screwdriver and the screw takes place at a location deeper in the recess 14 instead of a location at or close to the coronal end 10. This also may contribute to a better distribution of stresses.

Figure 12A:
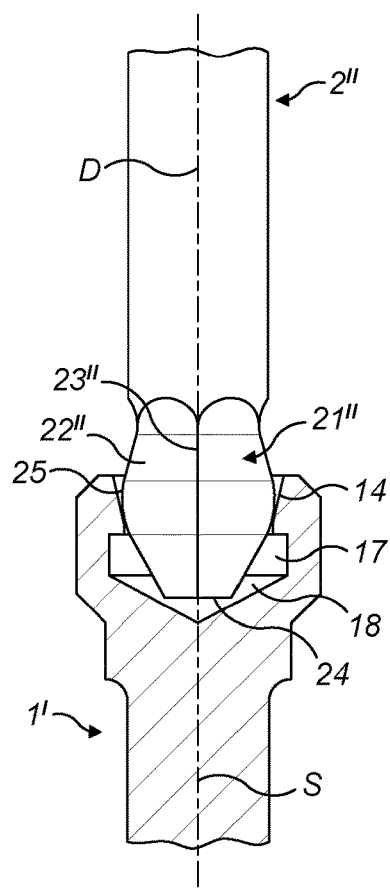
FIG. 12a shows a cross-sectional view of a still further embodiment of the combination of a screwdriver with a screw in a straight configuration of the screwdriver relative to the screw, the cross-section taken in a plane containing the screw axis.
Figure 12B:
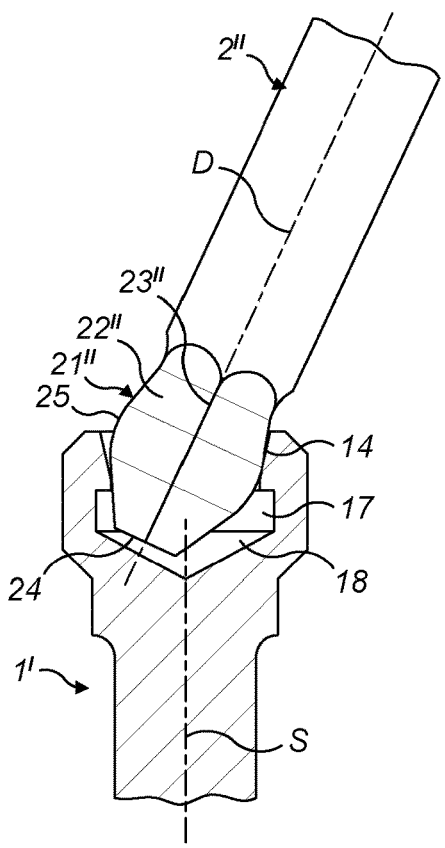
FIG. 12b shows a cross sectional view of the combination of FIG. 12a in a pivoted configuration of the screwdriver relative to the screw.

Referring to FIGS. 12a and 12b, a further embodiment of a screwdriver 2" is shown in combination with the screw. The screw corresponds to the screw 1' shown in FIGS. 6 to 11b. The screwdriver 2" comprises an engagement portion 21" that has in a plane including the drive axis D at least a portion 25 with a rounded or outwardly curved outer contour that continues into a tapered shape towards the free end 24. More in detail, the corners 23" of the polygon of the engagement portion are outwardly curved. Preferably, the corners 23" of the engagement portion 21" lie on a spherical segment in the portion 25. The outer surfaces 22" between the corners 23 are outwardly curved as in the previous embodiments. In use, when the engagement portion 21" engages the first recess 14 of the screw 1', it can pivot at an angle relative to the screw axis S while maintaining contact with the recess 14. The free end 24 of the engagement portion can extend into the bore 17 and the hollow cone 18, that provide space to allow the pivoting.

This embodiment enables a lifting function also at an angle with respect to the screw axis S.

Modifications of the above-described embodiments may be contemplated. First, the screw is not limited to the screw as shown in the embodiments. Various types of screws, various types of threads 12 or other engagement features may be provided. The head 3 of the screw can be spherical, tapered or otherwise shaped or can be omitted, so that the screw is headless. The bore 17 and the hollow cone 18 can be formed otherwise or can be omitted. While a hexagon recess is shown for the first recess 14, any other polygon may also work. The shape of the tapered recesses 5 may vary, in particular the intersection between the sidewalls and the tapered second recesses need not be curved. Similarly, the engagement portion 21 of the screwdriver may vary. The outwardly curved surfaces 22 between the corners may have in a plane perpendicular to the drive axis an arc-shape without being circular. The surfaces may be only partially circular. Also a combination of flat and circular or arc-shape portions is possible, as long as the surfaces have an outward curvature relative to line connecting adjacent corners.

The features of the screw driver and screw of different embodiments described can also be mixed and matched among the embodiments.

Moreover, in still further embodiments, the cooperating surfaces of the engagement portion of the screw driver and of the first recess of the screw may be inverted with respect to their shape to achieve the same or similar effects. For example, the screw may have a projection with a polygonal outer shape with curved outer surfaces and the screw driver may have a corresponding engagement portion with a polygonal engagement recess as shown in the embodiments of the screw. Alternatively, the first recess of the screw may have inwardly curved sidewalls and the engagement portion of the screw driver may have flat outer surfaces.

The invention claimed is:

1. A screwdriver for medical applications, the screwdriver comprising:
a shaft defining a longitudinal axis of the screwdriver, and
an engagement portion for engagement with a first recess of a screw, the engagement portion having a polygonal outer contour with corners and outer surfaces between the corners, wherein in a radial plane that is perpendicular to the longitudinal axis, the outer surfaces between two neighbouring corners are curved radially outward in a convex shape, wherein the engagement portion has a free end opposite to the shaft and wherein at least a portion of the engagement portion tapers towards the free end to permit holding of the screw when engaging the first recess of the screw, wherein the outer surfaces of the screwdriver are configured such that when the screwdriver is in use with the engagement portion engaging the first recess of the screw, contact between the screwdriver and the screw takes place at contact points along intersections formed between sidewalls of the first recess and a second recess associated with each sidewall, thereby contacting the screw at locations deeper in the first recess instead of locations at a coronal end of the first recess, and wherein a wedging takes place at the contact points so the screw is lifted and can be carried by the screwdriver,
wherein the screw has an apical end, a coronal end, and a longitudinal screw axis, the first recess being located at the coronal end for engagement with the screwdriver, the second recesses being provided in the sidewalls of the first recess, the second recesses tapering from the coronal end of the screw in the direction of the apical end, the first recess having a polygonal inner contour in a radial plane that is perpendicular to the longitudinal screw axis,
wherein the sidewalls between neighbouring corners of the first recess are flat and extend parallel to the longitudinal screw axis,
wherein the second recesses are provided at the center of each sidewall in a circumferential direction around the screw axis and wherein a width of the second recesses in the circumferential direction is smaller than a width of the sidewalls so that each of the intersections are formed between one of the sidewalls and an associated second recess, and
wherein when the engagement portion of the screwdriver engages the first recess and the corners of the polygon of the first recess are aligned with the corners of the polygon of the screwdriver, the contact between the engagement portion and the first recess is established at contact areas located along the intersection.

2. The screwdriver of claim 1, wherein in the radial plane, the outer surfaces are curved in a continuous arc shape.

3. The screwdriver of claim 1, wherein in the radial plane, the outer surfaces have a shape of a segment of a circle.

4. The screwdriver of claim 1, wherein in the radial plane, the outer surfaces comprise at least two straight portions that are connected to each other and that include an obtuse angle with each other.

5. The screwdriver of claim 4, wherein the obtuse angle is greater than an angle of the corners that define the polygon of the engagement portion.

6. The screwdriver of claim 1, wherein the engagement portion has in a plane including the longitudinal axis of the shaft at least a portion with a rounded outer contour to permit pivoting in the first recess of the screw.

7. A combination of a screwdriver and a screw for medical applications, in particular for dental applications, wherein the screwdriver is the screwdriver of claim 1 and wherein the engagement portion and the first recess are sized such that when the engagement portion engages the first recess and the corners of the engagement portion are aligned with the corners of the polygon of the first recess a clearance between the sidewalls of the polygon of the first recess and the outer surfaces of the engagement portion is greater in a region adjacent to the corners of the first recess than at a distance from the corners of the first recess.

8. A combination of a screwdriver and a screw for medical applications, in particular for dental applications, wherein the screwdriver is the screwdriver of claim 1 and
wherein the engagement portion has in a plane including the longitudinal axis of the shaft at least a portion with a rounded outer contour and wherein the engagement portion and the first recess are sized such that when the engagement portion engages the first recess the engagement portion is permitted to pivot in the first recess of the screw.

9. A combination of a screwdriver and a screw for medical applications, in particular for dental applications,
the screwdriver comprising:
   a shaft defining a longitudinal axis of the screwdriver; and
   an engagement portion for engagement with a first recess of the screw, the engagement portion having a polygonal outer contour with corners and outer surfaces between the corners, wherein in a radial plane that is perpendicular to the longitudinal axis, at least a proportion of the outer surfaces between two neighbouring corners are curved radially outward,
wherein the screw has an apical end, a coronal end, a longitudinal screw axis, a first recess at the coronal end for engagement with the screwdriver and a plurality of second recesses that are provided in the sidewalls of the first recess and that taper from the coronal end of the screw in the direction of the apical end, the first recess having a polygonal inner contour in a radial plane that is perpendicular to the longitudinal screw axis,
   wherein the sidewalls between neighbouring corners of the first recess are flat and extend parallel to the longitudinal screw axis,
wherein the second recesses are provided at the center of each sidewall in a circumferential direction around the screw axis and wherein a width of the second recesses in the circumferential direction is smaller than a width of the sidewalls so that an intersection is formed between each sidewall and an associated second recess, and
wherein when the engagement portion engages the first recess and the corners of the polygon of the first recess are aligned with the corners of the polygon of the screwdriver, the contact between the engagement portion and the first recess is established at contact areas located along the intersection.

10. The combination of claim 9, wherein a width of the second recesses in the circumferential direction decreases in the direction towards the apical end.

* * * * *